United States Patent [19]

Skinner et al.

[11] Patent Number: 5,900,502
[45] Date of Patent: May 4, 1999

[54] FLUORINATION PROCESS

[75] Inventors: Christopher John Skinner; John Hutchinson; Julie Thomson; Richard Dickinson Chambers, all of Durham, United Kingdom

[73] Assignee: BNFL Fluorochemicals Limited, United Kingdom

[21] Appl. No.: 08/656,366

[22] PCT Filed: Dec. 12, 1994

[86] PCT No.: PCT/GB94/02732

§ 371 Date: Oct. 25, 1996

§ 102(e) Date: Oct. 25, 1996

[87] PCT Pub. No.: WO95/16649

PCT Pub. Date: Jun. 22, 1995

[30] Foreign Application Priority Data

Dec. 16, 1993 [GB] United Kingdom .................. 9325757

[51] Int. Cl.$^6$ .......................... C07C 255/50; C07C 69/76
[52] U.S. Cl. .......................... 558/303; 560/8; 562/125; 562/840; 568/812; 568/936; 570/143; 570/147
[58] Field of Search ................. 558/303; 560/8; 562/125, 840; 568/812, 936; 570/143, 147

[56] References Cited

U.S. PATENT DOCUMENTS 5,212,301  5/1993  Moilliet et al. ................. 540/450

FOREIGN PATENT DOCUMENTS

0018606 A1  11/1980  European Pat. Off. .
0566268 A1  10/1993  European Pat. Off. .

*Primary Examiner*—Alan L. Rotman
*Assistant Examiner*—Charanjit S. Aulakh
*Attorney, Agent, or Firm*—Sheridan Ross P.C.

[57] ABSTRACT

According to the present invention there is provided a process for the selective introduction of one or more fluorine atoms into a disubstituted aromatic compound in an acid medium with fluorine gas characterized in that the acid medium has a dielectric constant of at least 20 and a pH of less than 3. The present process provides a cost effective means of selectively introducing one or more fluorine atoms into an aromatic compound in good overall yield.

20 Claims, No Drawings

FLUORINATION PROCESS

This application is 371 of PCT/GB94/02732, filed Dec. 12, 1994, which is now published as WO95/16649 on Jun. 22, 1995.

This invention relates to a process for the fluorination of aromatic compounds.

Processes for the fluorination of aromatic compounds are known where fluorine gas is used as a fluorinating agent but the strong oxidising properties of fluorine cause the aromatic compound to decompose and poor yields of the required products are obtained. The dilution of the fluorine gas with an inert gas, such as nitrogen, is described in EP-A2-0512715 and this moderates the oxidising effect of the fluorine allowing the introduction of one fluorine atom into the aromatic compound in good yield. Known processes for the preparation of polyfluoroaromatic compounds involves using more severe fluorinating conditions with a consequent increase in the formation of decomposition products or involves halogen exchange or reaction of an aromatic compound with a fluorinating agent such as cobalt trifluoride.

The direct fluorination of certain aromatic compounds in acetonitrile is known but is generally inconvenient because low reaction temperatures are required. Further problems occur where fluorination is carried out in solvents such as acetonitrile since reaction with the solvent leading to tar formation can occur.

The object of the present invention is to provide a fluorination process for making specific fluorinated compounds by the selective introduction of one or more fluorine atoms into an aromatic compound in good overall yield which may be operated at easily obtainable temperatures and which minimises reaction between fluorine and the solvent.

According to the present invention there is provided a process for the selective introduction of one or more fluorine atoms into a disubstituted aromatic compound by reaction of the aromatic compound in an acid medium with fluorine gas characterised in that the acid medium has a dielectric constant of at least 20 and a pH of less than 3.

The present process provides a cost effective means of selectively introducing one or more fluorine atoms into an aromatic compound in good overall yield.

The aromatic compound is preferably benzene which may be substituted by from one to five substituents. Suitable substituents may be independently selected from alkyl, alkoxy, halogen, —CN, —OH, —NO$_2$, —N(alkyl)$_2$, —NHCOalkyl, —COOalkyl, —COOH, —COalkyl, —CON(alkyl)$_2$, —COY, —CY$^1{}_3$ and —SO$_2$Y$^2$ in which Y is —H, —F, —Cl, —Br, Y$^1$ is —F or —Cl, and Y$^2$ is —F, —Cl, —Br, —N(alkyl)$_2$. In each of these substituents alkyl is preferably C$_{1-4}$-alkyl, alkoxy is preferably C$_{1-4}$-alkoxy and halogen is preferably —F, —Cl or Br.

Preferred substituents for the aromatic compound are selected from —CN, —OH, —NO$_2$, —NHCOCH$_3$, —OCH$_3$, —COOCH$_3$, —COOH, —COCH$_3$, —CH$_3$, —Cl, —Br and —F and combinations thereof. The aromatic compound is preferably disubstituted in the 1- and 4-positions or in the 1- and 2-positions and more preferably disubstituted in the 1- and 4-positions.

Where the aromatic compound is disubstituted the 1-position is preferably occupied by a meta-directing group and the 2- or 4-position is preferably occupied by an ortho/para-directing group.

In a preferred embodiment of the present invention the aromatic compound is of Formula (1):

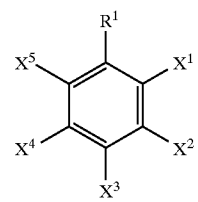

Formula (1)

wherein:
R$^1$ is a meta-directing group;
X$^1$, X$^3$ and X$^5$ each independently is —H, —F or an ortho/para-directing group;
X$^2$ and X$^4$ each independently is —H, halogen;
provided that at least one of X$^1$, X$^2$, X$^3$, X$^4$, X$^5$ is —H.

The meta-directing group represented by R$^1$ is preferably selected from —Br, —Cl, —F, —NO$_2$, —CN, —COY, —CY$^1{}_3$ and —SO$_2$Y$^2$ in which Y is —H, —F, —Cl, —Br, —C$_{1-4}$-alkyl, —OH or —OC$_{1-4}$-alkyl;
Y$^1$ is —F or —Cl;
Y$^2$ is —F, —Cl, —Br, —NH$_2$, —NH(C$_{1-4}$-alkyl) and —NH(C$_{1-4}$-alkyl)$_2$.

The ortho/para-directing groups represented by X$^1$, X$^3$ and X$^5$ are preferably selected from —OH, —OC$_{1-6}$-alkyl, C$_{1-6}$-alkyl and —NHCOC$_{1-6}$-alkyl.

Where one of the groups represented by X$^2$ and X$^4$ is halogen it is preferably —F or —Cl and where any of these groups are alkyl, alkoxy, —NH(alkyl) or —N(alkyl)$_2$ it is preferred that each alkyl or alkoxy contains from 1 to 6 carbon atoms.

Compounds of Formula (1) are preferably those in which R$^1$ is a meta-directing group, one of X$^1$, X$^3$ or X$^5$ is an ortho/para-directing group or —F and X$^2$ and X$^4$ are hydrogen, more preferably those in which R$^1$ is a meta-directing group, X$^3$ is an ortho/para-directing group or —F and X$^1$, X$^2$, X$^4$ and X$^5$ are hydrogen.

Especially preferred compounds of Formula (1) are those in which R$^1$ is selected from —CN, —NO$_2$, —COOCH$_3$, —COOH, —COCH$_3$, —Br, —Cl and —F, X$^3$ is selected from —OH, —OCH$_3$, —CH$_3$, —NHCOCH$_3$ and —F and X$^1$, X$^2$, X$^4$ and X$^5$ are hydrogen.

The acid medium preferably has a dielectric constant from 20 to 90, more preferably from 30 to 90, especially from 50 to 90. The acid medium preferably has a pH of less than 3, more preferably less than 2 and especially less than 1.

The acid medium is preferably selected from formic and sulphuric acids and oleum. Where the acid medium is formic or sulphuric acid it may contain water preferably from 5 to 0% water, more preferably from 2 to 0% water and especially from 1 to 0% water. Where the acid medium is oleum it is preferably from 1% to 30% oleum more preferably from 20% to 30% oleum. Inert diluents, particularly fluorinated solvents such as 'ARKLONE' P (ARKLONE is a trade mark of ICI PLC) may be present in the acid medium such solvents should be substantially free from water. The acid medium is preferably sulphuric or formic acid, more preferably from 95% to 100% sulphuric acid, more preferably from 95% to 97% formic acid and especially from 96% to 97% formic acid.

The use of from 98% to 100% sulphuric or particularly from 95% to 97% formic acid as the acid medium is advantageous where multiple fluorine atoms are to be introduced into the aromatic compound because such acids allow high conversion of the aromatic compound of Formula (1) to di-, tri-, tetra- and penta-fluorinated derivatives.

The process may be carried out at a temperature from 10° C. to 90° C., preferably at a temperature from 10° C. to 40° C. and especially from 10° C. to 20° C.

The fluorine gas is preferably diluted before use by mixing with an inert gas such as nitrogen or helium. The concentration of fluorine in inert gas is preferably from 1% to 50% by volume, more preferably from 2% to 25% and especially from 5% to 15%.

The ratio of fluorine to aromatic compound may be varied within wide limits although it is preferred that the molar ratio of fluorine to aromatic compound is from 1.2:1 to 6:1, depending on the degree of fluorination required. Use of the higher ratio of fluorine to aromatic compound ensures that multiple fluorine atoms are introduced into the aromatic compound forming polyfluorinated products.

When fluorination is substantially complete the fluorinated product(s) may be isolated by purging the reaction mixture with nitrogen to remove any residual fluorine and hydrogen fluoride followed by dilution with excess water and extraction into a suitable solvent followed by distillation. The fluorinated products may be separated by fractional distillation or by crystallisation from a suitable solvent.

Under the above process conditions a mixture of products is obtained where one or more fluorine atoms have been introduced into the aromatic compound. For example when 4-fluorobenzoic acid is the aromatic compound and 98% sulphuric acid is used as the acid medium the mixture of products obtained comprises 2,4- and 3,4-difluoro-, 2,4,5-, 2,3,4- and 3,4,5-trifluoro-, 2,3,4,5-tetrafluoro- and 2,3,4,5,6-pentafluorobenzoic acids.

The present process thus offers a convenient synthetic route to mono- and polyfluorinated aromatic compounds which are difficult to prepare by other processes or may only be prepared in poor yield and minimises the need to dispose of waste fluorinated tars and other by-products. The mono- and polyfluorinated products find uses as synthetic intermediates in the preparation of agrochemicals and pharmaceuticals.

The invention is further illustrated by the following examples.

A comparative example, Example A, is provided to illustrate the effect of replacing the acid medium by an organic solvent (acetonitrile) in which only one fluorine atom is introduced in relatively poor yield into the starting material. No more highly fluorinated aromatic could be isolated from the reaction mixture.

EXAMPLE 1

Fluorination of 4-Cyanophenol

A stirred reaction vessel charged with 4-cyanophenol (11.9 g, 0.1 mol) and 96% formic acid (200 cm$^3$) was purged with nitrogen and cooled to 10° C. Fluorine (0.2 mol), diluted with nitrogen to 10%, was passed through the cooled, stirred solution over a period of about 6 hours. The vessel was purged with nitrogen and allowed to warm to ambient temperature. The reaction mixture was poured into water and extracted with diethyl ether. The extracts were dried and the solvent was removed by distillation to leave a tan solid (12.4 g). Short path distillation of the crude product (3.9 g) at reduced pressure gave an off white solid (3.4 g) which was shown to comprise three main compounds by nmr and GC analysis. The mixture was shown to contain 4-cyano-2-fluorophenol ($\delta_F$-134.7 ppm[$d_6$-Me$_2$CO]) and 4-cyano-2,6-difluorophenol ($\delta_F$-131.0 ppm[$d_6$-Me$_2$CO]) in yields of 64% and 10%, respectively, with a conversion of 84%. (NB The chemical shifts in this and all other examples were relative to CFCl$_3$.)

EXAMPLE 2

Fluorination of 4-Nitrophenol

In a similar manner to that described in Example 1, 0.2 mol fluorine diluted with nitrogen to 10% was passed through a solution of 4-nitrophenol (0.1 mol) in 96% formic acid over 4.5 hours at 10° C. The reaction mixture was poured into water and extracted with diethylether. The ether solution was dried and the solvent removed using a rotary evaporator to leave a brown liquid. This was transferred to a short path distillation apparatus and distilled at reduced pressure to yield pale yellow crystals (12.9 g). GC/MS and $^{19}$Fnmr (CDCl$_3$) analysis showed these to be mainly unreacted starting material, 2-fluoro-4-nitrophenol [(M$^+$157, $\delta_F$-137.5 ppm, yield 70%), and 2,6-difluoro-nitrophenol (M$^+$175, $\delta_F$-131.7 ppm, yield 7%). The conversion was 75%.

EXAMPLE 3

Fluorination of 4-Nitroacetanilide

By the method outlined in Example 1, 4-nitroacetanilide was fluorinated to give 2-fluoro-4-nitroacetanilide (M$^+$198, $\delta_F$-125.8 ppm [CDCl$_3$], yield 60%) and 2,6-difluoro-4-nitroacetanilide ($\delta_F$-112.8 ppm [CDCl$_3$], yield 8%). Conversion 100%.

EXAMPLE 4

Fluorination of Methyl 4-methoxybenzoate

By the method outlined in Example 1, methyl 4-methoxybenzoate was fluorinated to give methyl 3-fluoro-4-methoxybenzoate (M$^+$184, $\delta_F$-135.3 ppm [CDCl$_3$], yield 50%) and methyl 3,5-difluoro-4-methoxybenzoate (M$^+$202, $\delta_F$-128.3 ppm [CDCl$_3$], yield 10%). Conversion 90%.

EXAMPLE 5

Fluorination of 4-Methoxybenzonitrile

By the method outlined in Example 1, 4-methoxybenzonitrile was fluorinated to give 3-fluoro-4-methoxybenzonitrile ($\delta_F$-125.8 ppm [CDCl$_3$], yield 35%) and 3,5-difluoro-4-methoxybenzonitrile ($\delta_F$-132.5 ppm [CDCl$_3$], yield 10%). Conversion 90%.

EXAMPLE 6

Fluorination of 4-Hydroxyacetophenone

By the method outlined in Example 1, 4-hydroxyacetophenone was fluorinated to give 3-fluoro-4-hydroxyacetophenone ($\delta_F$-133.1 ppm [$d_6$-Me$_2$CO], yield 40%) and 3,5-difluoro-4-hydroxyacetophenone ($\delta_F$-132.9 ppm [$d_6$-Me$_2$CO], yield 7%). Conversion 83%

EXAMPLE 7

Fluorination of Methyl 4-hydroxybenzoate

By the method outlined in Example 1, methyl 4-hydroxybenzoate was fluorinated to give methyl 3-fluoro-4-hydroxybenzoate ($\delta_F$-133.2 ppm [$d_6$-Me$_2$CO], yield 30%) and methyl 3,5-difluoro-4-hydroxybenzoate ($\delta_F$-129.1 ppm [$d_6$-Me$_2$CO], yield 17%). Conversion 100%.

EXAMPLE 8

Fluorination of 4—Nitrotoluene

By the method outlined in Example 1, 4-nitrotoluene was fluorinated to give 2-fluoro-4-nitrotoluene (M$^+$155, $\delta_F$-113.4 ppm [CDCl$_3$], yield 50%) and a trace of 2,6-difluoro-4-nitrotoluene (M$^+$173, $\delta_F$-110.2 ppm [CDCl$_3$]). Conversion 63%.

EXAMPLE 9

Fluorination of 4-Nitroanisole

By the method outlined in Example 1, 4-nitroanisole was fluorinated to give 2-fluoro-4-nitroanisole (M$^+$171, $\delta_F$-131.6 ppm [CDCl$_3$], yield 50%) and 2,6-difluoro-4-nitroanisole (M$^+$189, $\delta_F$-125.1 ppm [CDCl$_3$], yield 20%). Conversion 60%.

EXAMPLE 10

Fluorination of 4-cyanotoluene

By the method outlined in Example 1, p-tolunitrile was fluorinated to give 4-cyano-2-fluorotoluene (M$^+$135, $\delta_F$-114.5 ppm [CDCl$_3$], yield 60%) and 4-cyano-2,6-difluorotoluene (M$^+$153, $\delta_F$-111.1 ppm [CDCl$_3$], yield 2%). Conversion 86%.

EXAMPLE 11

Fluorination of 4-Chloroanisole

By the method outlined in Example 1, 4-chloroanisole was fluorinated to give 4-chloro-2-fluoroanisole (M$^+$160, $\delta_F$-132.7 ppm [CDCl$_3$], yield 50%) and 4-chloro-2,6-difluoroanisole (M$^+$178, $\delta_F$-127.1 ppm [CDCl$_3$], yield 7%). Conversion 80%.

Fluorinations of 4-Fluorobenzoic acid

In each of the following examples the mixtures of fluoro and polyfluorobenzoic acids were analysed first, by comparison of the 19$_F$nmr spectra of the mixtures, with the spectra of authentic samples. More accurate quantitative analysis of the components in these mixtures was obtained by conversion of the carboxylic acids to their more volatile silyl esters, by treatment with bis(trimethylsilyl)acetamide (BSA) and then analysis of g.c./mass spec. Therefore the quoted mass-spectrometry data refers to the corresponding silyl esters.

EXAMPLE 12

Formic acid (substrate to fluorine ratio 1:1.6)

A solution containing 4-fluorobenzoic acid (11.5 g, 82.1 mmol) in 96% formic acid (200 cm$^3$) was placed in a fluorination apparatus with attached soda lime filled drying tube. Fluorine gas (133 mmol) as a 10% mixture in nitrogen was then passed through the stirred solution using narrow bore PTFE tubing at ca 60 cm$^3$/min$^{-1}$. The mixture was added to an excess of water (1000 cm$^3$) and the resulting solid product was filtered off under vacuum. The filtrate was then extracted with dichloromethane (3×50 cm$^3$). After drying (MgSO$_4$), the dichloromethane was removed under vacuum and an off-white solid resulted (10.5 g).

Analysis of the resulting solid by $^{19}$Fnmr against an external standard of fluorobenzene (7.3 g, 50.1 mmol) showed a conversion of 32% from 4-fluorobenzoic acid. The product contained 4-fluorobenzoic acid (7.8 g), $\delta$F -104.2, electron impact, m/z 212 (M$^+$, 3.2%), 197 (—CH$_3$, 100%); 3,4-difluorobenzoic acid (2.7 g), $\delta$F -128.7 and -136.5, electron impact, m/z 230 (M$^+$, 2.4%), 215 (—CH$_3$, 100%) and unidentified material (0.1 g).

EXAMPLE 13

Formic acid (substrate to fluorine ratio 1:2)

A solution containing 4-fluorobenzoic acid (11.5 g, 82.1 mmol) in 96% formic acid (200 cm$^3$) was placed in a fluorination apparatus with attached soda lime filled drying tube. Fluorine gas (165 mmol) as a 10% mixture in nitrogen was then passed through the stirred solution using narrow bore PTFE tubing at ca 60 cm$^3$/min$^{-1}$. The mixture was added to an excess of water (1000 cm$^3$) and the resulting solid product was filtered off under vacuum. The filtrate was then extracted with dichloromethane (3×50 cm$^3$). After drying (MgSO$_4$), the dichloromethane was removed under vacuum and an off-white solid resulted (8.8 g).

Analysis of the resulting solid by $^{19}$Fnmr against an external standard of fluorobenzene (10.2 g, 69.9 mmol) showed a conversion of 51.5% from 4-fluorobenzoic acid. The product contained 4-fluorobenzoic acid (5.6 g), $\delta$F -104.2, electron impact$_0$ m/z 212 (M$^+$, 3.24%), 197 (—CH$_3$, 100%); 3,4-difluorobenzoic acid (2.8 g,), $\delta$F -128.7 and -136.5, electron impact, m/z 230 (M$^+$, 2.40%), 215 (—CH$_3$, 100%) and unidentified material (0.4 g).

EXAMPLE 14

Formic acid (substrate to fluorine ratio 1:3)

A solution containing 4-fluorobenzoic acid (4.0 g, 28.2 mmol) in 96% formic acid (200 cm$^3$) was placed in a fluorination apparatus with attached soda lime filled drying tube. Fluorine gas (82.5 mmol) as a 10% mixture in nitrogen was then passed through the stirred solution using narrow bore PTFE tubing at ca 60 cm$^3$/min$^{-1}$. The mixture was added to an excess of water (1000 cm$^3$) and the resulting solid product was filtered off under vacuum. The filtrate was then extracted with dichloromethane (3×50 cm$^3$). After drying (MgSO$_4$), the dichloromethane was removed under vacuum and an off-white solid resulted (3.1 g).

Analysis of the resulting solid by $^{19}$Fnmr against an external standard of trifluorotoluene (1.7 g, 11.6 mmol) showed a conversion of 65.3% from 4-fluorobenzoic acid. The product contained 4-fluorobenzoic acid (1.4 g), $\delta$F -104.2, electron impact, m/z 212 (M$^+$, 3.2%), 197 (—CH$_3$, 100%); 3,4-difluorobenzoic acid (1.6 g,), $\delta$F -128.7 and -136.5, electron impact, m/z 230 (M$^+$, 2.4%), 215 (—CH$_3$, 100%) and unidentified material (0.2 g).

EXAMPLE 15

Formic acid (substrate to fluorine ratio 1:4)

A solution containing 4-fluorobenzoic acid (6.0 g, 42.9 mmol) in 96% formic acid (200 cm$^3$) was placed in a fluorination apparatus with attached soda lime filled drying tube. Fluorine gas (165 mmol) as a 10% mixture in nitrogen was then passed through the stirred solution using narrow bore PTFE tubing at ca 60 cm$^3$/min$^{-1}$. The mixture was added to an excess of water (1000 cm$^3$) and the resulting solid product was filtered off under vacuum. The filtrate was then extracted with dichloromethane (3×50 cm$^3$). After drying (MgSO$_4$), the dichloromethane was removed under vacuum and a white solid resulted (5.3 g).

Analysis of the resulting solid by $^{19}$Fnmr against an external standard of trifluorotoluene (5.7 g, 38.9 mmol) showed a conversion of 79.2% from 4-fluorobenzoic acid. The product contained 4-fluorobenzoic acid (1.2 g), $\delta$F -104.2, electron impact, m/z 212 (M$^+$, 3.2%), 197 (—CH$_3$, 100%); 3,4-difluorobenzoic acid (3.5 g), $\delta$F -128.7 and -136.5, electron impact, m/z 230 (M$^+$, 2.4%), 215 (—CH$_3$, 100%); 2,4,5-trifluorobenzoic acid (0.2 g), $\delta$F -108.2, -123.4 and -141.3, electron impact, m/z 248 (M$^+$, 1.2%), 233 (—CH$_3$, 100%); 2,3,4-trifluorobenzoic acid (0.1 g), $\delta$F -124.4, -128.7 and -158.7, electron impact, m/z 233

(—CH$_3$, 5.1%); 3,4,5-trifluorobenzoic acid (0.2 g), δF −132.6 and −151.3, electron impact, m/z 248 (M$^+$, 1.5%), 233 (—CH$_3$, 94.6%) and unidentified material (0.3 g).

EXAMPLE 16

Sulphuric acid (98%) (substrate to fluorine ratio 1:1.6)

A solution containing 4-fluorobenzoic acid (14.4, 102.9 mmol) in 98% sulphuric acid (150 cm$^3$) was placed in a fluorination apparatus with attached soda lime filled drying tube. Elemental fluorine (165 mmol) as a 10% mixture in nitrogen was then passed through the stirred solution using narrow bore PTFE tubing at ca 60 cm$^3$/min$^{-1}$. The resulting mixture was worked up by adding the mixture to an excess of water (1000 cm$^3$) and the resulting solid product was filtered off under vacuum. The filtrate was then extracted with dichloromethane (3×50 cm$^3$). After drying (MgSO$_4$), the dichloromethane was removed under vacuum and a white solid resulted (11.6 g).

Analysis of the resulting solid by $^{19}$Fnmr against an external standard of trifluorotoluene (mmol) showed a conversion of 82.6% from 4-fluorobenzoic acid. The product containing 4-fluorobenzoic acid (2.5 g), δF −104.2, electron impact, m/z 212 (M$^+$, 3.28%), 197 (—CH$_3$, 100%); 3,4-difluorobenzoic acid (6.8 g), δF −128.7 and −136.5, electron impact, m/z 230 (M$^+$, 2.76%), 215 (—CH$_3$, 100%); 2,4,5-trifluorobenzoic acid (1.3 g), δF −108.2, −123.3 and −141.2, electron impact, m/z 248 (M$^+$, 1.09%), 233 (—CH$_3$, 100%); 2,3,4-trifluorobenzoic (0.6 g), δF −124.3, −128.7 and −158.6, electron impact, m/z 248 (M$^+$, 2.29%), 233 (—Cl$_3$, 93.90%); 3,4,5-trifluorobenzoic acid (0.3 g), δF −132.6 and −151.2, electron impact, m/z 248 (M$^+$, 1.31%), 233 (—CH$_3$, 100%) and unidentified material (0.2 g).

EXAMPLE 17

Sulphuric acid (98%) (substrate to fluorine ratio 1:2)

A solution containing 4-fluorobenzoic acid (11.5 g, 82.5 mmol) in 98% sulphuric acid (150 cm$^3$) was placed in a fluorination apparatus with attached soda lime filled drying tube. Elemental fluorine (165 mmol) as a 10% mixture in nitrogen was then passed through the stirred solution using narrow bore PTFE tubing at ca 60 cm$^3$/min$^{-1}$. The resulting mixture was worked up by adding the mixture to an excess of water (1000 cm$^3$) and the resulting solid product was filtered off under vacuum. The filtrate was then extracted with dichloromethane (3×50 cm$^3$). After drying (MgSO$_4$), the dichloromethane was removed under vacuum and a white solid resulted (10.6 g).

Analysis of the resulting solid by $^{19}$Fnmr against an external standard of trifluorotoluene (3.2 g, 21.8 mmol) showed a conversion of 34.8% from 4-fluorobenzoic acid. The product containing 4-fluorobenzoic acid (1.8 g), δF −104.2, electron impact, m/z 212 (M$^+$, 3.3%), 197 (—CH$_3$, 100%); 3,4-difluorobenzoic acid (6.2 g), δF −128.7 and −136.5, electron impact, m/z 230 (M$^+$, 2.8%), 215 (—CH$_3$, 100%); 2,4,5-trifluorobenzoic acid (0.3 g), δF −108.2, −123.3 and −141.2, electron impact, m/z 248 (M$^+$, 1.1%), 233 (—CH$_3$, 100%); 2,3,4-trifluorobenzoic (0.4 g), δF −124.3, −128.7 and −158.6, electron impact, m/z 248 (M$^+$, 2.3%), 233 (—CH$_3$, 93.9%); 3,4,5-trifluorobenzoic (0.4 g), δF-132.6 and −151.2, electron impact, m/z 248 (M$^+$, 1.3%), 233 (—CH$_3$, 100%); 2,3,4,5-tetrafluorobenzoic acid (0.7 g), δF-133.3, −137.9, −142.7 and −151.2, electron impact, m/z 266 (M$^+$, 0.5%), 251 (—CH$_3$, 60.3%) and unidentified material (0.4 g).

EXAMPLE 18

Sulphuric acid (98%) (substrate to fluorine ratio 1:3)

A solution containing 4-fluorobenzoic acid (7.7 g, 55.0 mmol) in 98% sulphuric acid (150 cm$^3$) was placed in a fluorination apparatus with attached soda lime filled drying tube. Elemental fluorine (165 mmol) as a 10% mixture in nitrogen was then passed through the stirred solution using narrow bore PTFE tubing at ca 60 cm$^3$/min$^{-1}$. The resulting mixture was worked up by adding the mixture to an excess of water (1000 cm$^3$) and the resulting solid product was filtered off under vacuum. The filtrate was then extracted with dichloromethane (3×50 cm$^3$). After drying (MgSO$_4$), the dichloromethane was removed under vacuum and a white solid resulted (5.9 g).

Analysis of the resulting solid by $^{19}$Fnmr against an external standard of trifluorotoluene (3.6 g, 24.9 mmol) showed a conversion of 92.3% from 4-fluorobenzoic acid. The product contained 4-fluorobenzoic acid (0.6 g), δF −104.2, electron impact, m/z 212 (M$^+$, 3.28%), 197 (—CH$_3$, 100%); 3,4-difluorobenzoic acid (3.4 g), δF −128.7 and −136.5, electron impact, m/z 230 (M$^+$, 2.8%), 215 (—CH$_3$, 100%); 2,4,5-trifluorobenzoic acid (0.6 g), δF −108.2, −123.3 and −141.2, electron impact, m/z 248 (M$^+$, 1.1%), 233 (—CH$_3$, 100%); 2,3,4-trifluorobenzoic acid (0.2 g), δF −124.3, −128.7 and −158.6, electron impact, m/z 248 (M$^+$, 2.3%), 233 (—CH$_3$, 93.9%); 3,4,5-trifluorobenzoic acid (0.5 g), δF −132.6 and −151.2, electron impact m/z 248 (M$^+$, 1.3%), 233 (—CH$_3$, 100%); 2,3,4,5-tetrafluorobenzoic acid (0.3 g), δF −133.3, -137.9, −142.7 and −151.2, electron impact, m/z 266 (M$^+$, 0.5%), 251 (—CH$_3$, 60.3%) and unidentified material (0.3 g).

Comparative Example A

Fluorination of 4-Fluorobenzoic Acid in Acetonitrile

A solution containing 4-fluorobenzoic acid (1.6 g, 11.3 mmol) in acetonitrile (80 cm$^3$) was placed in a fluorination apparatus fitted with a tube filled with soda lime. Fluorine gas (35 mmol) as a 10% mixture in nitrogen was then passed through the stirred solution at 25° C. using narrow bore PTFE tubing at ca 4.0 cm$^3$/min$^{-1}$. The mixture was added to an excess of water (500 cm$^3$) followed by extraction with dichloromethane (3×25 cm$^3$). After drying (MgSO$_4$), dichloromethane was removed under vacuum leaving brown solid (1.6 g).

Analysis of the solid by $^{19}$Fnmr after preparing the silyl ester derivatives by reacting the product with bis trimethylsilyl acetamide against an external standard of fluorobenzene (0.2 g, 3.9 mmol) showed a conversion of 85% from 4-fluorobenzoic acid. The product contained 4-fluorobenzoic acid, δF −104.4, electron impact, m/z 212 (M$^+$, 3.5%), 197 (—CH$_3$, 100%) and 3,4-difluorobenzoic acid, 66%, δF −128.8 and −136.7, electron impact, m/z 230 (M$^+$, 2.6%), 215 (—CH$_3$, 100%) in a ratio of 33% to 66% and unidentified material.

EXAMPLE 19

Fluorination of 4-Fluorobenzoic Acid in Formic Acid

A solution containing 4-fluorobenzoic acid (1.6 g, 11.3 mmol) in 98% formic acid (80 cm$^3$) was placed in a fluorination apparatus fitted with a tube filled with soda lime. Fluorine gas (35 mmol) as a 10% mixture in nitrogen was then passed through the stirred solution at 25° C. using narrow bore PTFE tubing at ca 4.0 cm$^3$/min$^{-1}$. The mixture was added to an excess of water (500 cm$^3$) followed by extraction with dichloromethane (3×25 cm$^3$). After drying (MgSO$_4$), dichloromethane was removed under vacuum leaving an off-white solid (0.7 g).

Analysis of the solid by $^{19}$Fnmr after preparing the silyl ester derivatives by reacting the product with bis trimethylsilyl acetamide against an external standard of fluorobenzene (0.2 g, 3.9 mmol) showed a conversion of 98% from 4-fluorobenzoic acid. The product contained 4-fluorobenzoic acid, δF -104.2, electron impact, m/z 212 (M$^+$, 3.2%), 197 (—CH$_3$, 100%); 3,4-difluorobenzoic acid, δF -128.7 and -135.5, electron impact, m/z 230 (M$^+$, 2.4%), 215 (—CH$_3$, 100%); 2,4,5-trifluorobenzoic acid, δF -108.2, 123.4 and -141.3, electron impact, m/z 248 (M$^+$, 1.2%), 233 (—CH$_3$, 100%); 2,3,4-trifluorobenzoic, δF -124.4, -128.7 and -158.7, electron impact, m/z 233 (—CH$_3$, 5.1%) and 3,4,5-trifluorobenzoic acid, δF -132.6 and -151.3, electron impact, m/z 248 (M$^+$, 1.5%), 233 (—CH$_3$, 94.6%) in a ratio of 8%:73%:8%:4%:7% and unidentified material.

EXAMPLE 20

Fluorination of 4-Fluorobenzoic Acid in Sulphuric Acid (98%)

A solution containing 4-fluorobenzoic acid (1.6 g, 11.3 mmol) in 98% sulphuric acid (80 cm$^3$) was placed in a fluorination apparatus fitted with a tube filled with soda lime. Fluorine gas (35 mmol) as a 10% mixture in nitrogen was then passed through the stirred solution at 25° C. using narrow bore PTFE tubing at ca 4.0 cm$^3$/min$^{-1}$. The mixture was added to an excess of water (500 cm$^3$) followed by extraction with dichloromethane (3×25 cm$^3$). After drying (MgSO$_4$), dichloromethane was removed under vacuum leaving an off-white solid (1.3 g).

Analysis of the solid by $^{19}$Fnmr after preparing the silyl ester derivatives by reacting the product with bis trimethylsilyl acetamide against an external standard of fluorobenzene (0.2 g, 2.3 mmol) showed a conversion of 97% from 4-fluorobenzoic acid. The product contained 4-fluorobenzoic acid, δF -104.2, electron impact, m/z 212 (M$^+$, 3.3%), 197 (—CH$_3$, 100%); 2,4-difluorobenzoic acid, δF -97.6, -100.0; 3,4-difluorobenzoic acid, δF -128.7 and -136.5, electron impact, m/z 230 (M$^+$, 2.8%), 215 (—CH$_3$, 100%) ; 2,4,5-trifluorobenzoic acid, δF -108.2, -123.3 and -141.2, electron impact, m/z 248 (M$^+$, 1.1%), 233 (—CH$_3$, 100%); 2,3,4-trifluorobenzoic, δF -124.3, -128.7 and -158.6, electron impact, m/z 248 (—CH$_3$, 2.3%); 3,4,5-trifluorobenzoic acid, δF -132.6 and -151.2, electron impact, m/z 248 (M$^+$, 1.3%), 233 (—CH$_3$, 100%); 2,3,4,5-tetrafluorobenzoic acid, δF -133.3, -137.9, -142.7 and -151.2, electron impact, m/z 266 (M$^+$, 0.5%), 251 (—CH$_3$, 60.3%); 2,3,4,5,6-pentafluorobenzoic acid, δF -136.9, -146.8 and -158.6, electron impact, m/z 269 (—CH$_3$, 0.9%) in a ratio of 6%:2%:61%:9%:6%:9%:6%:1% and unidentified material.

EXAMPLE 21

Fluorination of 4-Fluorobenzoic Acid in Oleum (30%. SO$_3$)

A solution containing 4-fluorobenzoic acid (1.6 g, 11.3 mmol) in 30% oleum (80 cm$^3$) was placed in a fluorination apparatus fitted with a tube filled with soda lime. Fluorine gas (35 mmol) as a 10% mixture in nitrogen was then passed through the stirred solution at 25° C. using narrow bore PTFE tubing at ca 4.0 cm$^3$/min$^{-1}$. The mixture was added to an excess of water (500 cm$^3$) followed by extraction with dichloromethane (3×25 cm$^3$). After drying (MgSO$_4$), dichloromethane was removed under vacuum leaving a white solid (1.3 g).

Analysis of the solid by $^{19}$Fnmr after preparing the silyl ester derivatives by reacting the product with bis trimethylsilyl acetamide against an external standard of fluorobenzene (0.4 g, 4.6 mmol) showed a conversion of 88% from 4-fluorobenzoic acid. The product contained 4-fluorobenzoic acid, δF -104.3, electron impact, m/z 212 (M$^+$, 3.4%), 197 (—CH$_3$, 100%); 3,4-difluorobenzoic acid, δF -128.9 and -136.5, electron impact, m/z 230 (M$^+$, 2.6%), 215 (—CH$_3$, 100%); 2,4,5-trifluorobenzoic acid, δF -108.2, -123.3 and -141.2, electron impact, m/z 248 (M$^+$, 1.3%), 233 (—CH$_3$, 100%); 2,3,4-trifluorobenzoic, δF -124.3, -128.7 and -158.6, electron impact, m/z 248 (—CH$_3$, 2.5%), 233 (—CH$_3$, 93.2%); 3,4,5-trifluorobenzoic acid, δF -132.7 and -151.5, electron impact, m/z 248 (M$^+$, 1.2%), 233 (—CH$_3$, 94.3%); 2,3,4,5-tetrafluorobenzoic acid, δF -133.3, -137.9, -142.7 and -151.2, electron impart, m/z 251 (—CH$_3$, 60.3%); 2,3,4,5,6-pentafluorobenzoic acid, δF -136.9, -146.8 and -158.6 in a ratio of 24%:55%:5%:4%:8%:3%:1% and unidentified material.

We claim:

1. A process for the selective introduction of one or more fluorine atoms into an aromatic compound substituted with at least two substituents which are not hydrogen and having at least one position substituted only with hydrogen by reaction of the aromatic compound with fluorine gas in an acid medium having a dielectric constant of at least 20, a pH of less than 3 and containing less than 5% water, whereby said at least one position substituted only with hydrogen is replaced by fluorine.

2. A process according to claim 1 in which the acid medium is selected from formic and sulphuric acids and oleum.

3. A process according to claim 1 in which the fluorine gas is diluted with an inert gas.

4. A process according to claim 2 in which the acid medium is sulphuric or formic acid.

5. A process according to claim 2 in which the fluorine gas is diluted with an inert gas.

6. A process according to claim 4 in which the fluorine gas is diluted with an inert gas.

7. A process according to claim 4 wherein the acid medium contains at least 95% sulphuric acid or at least 95% formic acid.

8. A process according to claim 7 wherein the acid medium contains at least 96% sulphuric acid or at least 98% formic acid.

9. A process according to claim 1 wherein the substituents, which may be the same or different, are selected from the group consisting of alkyl, alkoxy, halogen, —CN, —OH, —NO$_2$, —N(alkyl)$_2$, —NHCOalkyl, —COO(alkyl), —COOH, —CO(alkyl), —CON(alkyl)$_2$, —COY, —CY$^1_3$ and —SO$_2$Y$^2$, wherein Y is —H, —F, —Cl, or —Br, Y$^1$ is —F or —Cl, and Y$^2$ is —F, —Cl, —Br, or —N(alkyl)$_2$.

10. A process according to claim 9 wherein the substituents are selected from the group consisting of —CN, —OH, —No$_2$, —NHCOCH$_3$, —OCH$_3$, —COOCH$_3$, —COOH, —COCH$_3$, —CH$_3$, —Cl, —Br and —F.

11. A process according to claim 1 wherein the aromatic compound is substituted in the 1-position with a meta-directing group and in the 2-position or 4-position with an ortho/para-directing group.

12. A process according to claim 1 wherein the aromatic compound is benzene.

13. A process according to claim 12 wherein the benzene is substituted with 2–5 substituents.

14. A process according to claim 13 wherein the substituents, which may be the same or different, are selected from the group consisting of alkyl, alkoxy, halogen, —CN, —OH, —NO$_2$, —N(alkyl)$_2$, —NHCOalkyl, —COO(alkyl), —COOH, —CO(alkyl), —CON(alkyl)$_2$, —COY, —CY$^1{}_3$ and —SO$_2$Y$^2$, wherein Y is —H, —F, —Cl, or —Br, Y$^1$ is —F or —Cl, and Y$^2$ is —F, —Cl, —Br, or —N(alkyl)$_2$.

15. A process according to claim 14 wherein the substituents are selected from the group consisting of —CN, —OH, —NO$_2$, —NHCOCH$_3$, —OCH$_3$, —COOCH$_3$, —COOH, —COCH$_3$, —CH$_3$, —Cl, —Br and —F.

16. A process according to claim 13 wherein the benzene has the following formula:

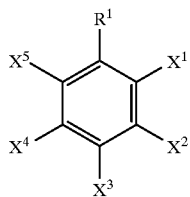

wherein:

R$^1$ is a meta-directing group;

X$^1$, X$^3$ and X$^5$ each independently is —H, —F or an ortho/para-directing group; and X$^2$ and X$^4$ each independently is —H or halogen; provided that at least one of X$^1$, X$^2$, X$^3$, X$^4$, X$^5$ is —H.

17. A process according to claim 16 wherein R$^1$ is —Br, —Cl, —F, —NO$_2$, —CN, —COY, —CY$^1{}_3$ or —SO$_2$Y$^2$, wherein Y is —H, —F, —Cl, —Br, —C$_{1-4}$-alkyl, —OH or —OC$_{1-4}$-alkyl, Y$^1$ is —F or —Cl, and Y$^2$ is —F, —Cl, —Br, —NH$_2$, —NH(C$_{1-4}$-alkyl) or —NH(C$_{1-4}$-alkyl)$_2$.

18. A process according to claim 16 wherein X$^1$, X$^3$ and X$^5$ each is independently —OH, —OC$_{1-6}$-alkyl, C$_{1-6}$-alkyl or —NHCOC$_{1-6}$-alkyl.

19. A process according to claim 16 wherein R$^1$ is —CN, —NO$_2$, —COOCH$_3$, —COOH, —COCH$_3$, —Br, —Cl or —F, X$^3$ is —OH, —OCH$_3$, —CH$_3$, —NHCOCH$_3$ or —F, and X$^1$, X$^2$, X$^4$ and X$^5$ each is hydrogen.

20. A process for the introduction of fluorine into the 3-position of an aromatic compound substituted with a meta-directing group at the 1-position and an ortho/para-directing group at the 4-position and having a hydrogen atom at the 3-position by reaction of the aromatic compound with fluorine gas in an acid medium having a dielectric constant of at least 20, a pH of less than 3 and containing less than 5% water, whereby the hydrogen atom at the 3-position is replaced by fluorine.

* * * * *